United States Patent
Rawal et al.

(10) Patent No.: US 10,971,258 B2
(45) Date of Patent: Apr. 6, 2021

(54) SYSTEMS, METHODS, AND APPARATUSES FOR MANAGING ADHERENCE TO A REGIMEN

(71) Applicants: Rajesh Rawal, Fullerton, CA (US); Sreenivasan Narayanan, Lincolnshire, IL (US)

(72) Inventors: Rajesh Rawal, Fullerton, CA (US); Sreenivasan Narayanan, Lincolnshire, IL (US)

( * ) Notice: Subject to any disclaimer, the term of this patent is extended or adjusted under 35 U.S.C. 154(b) by 0 days.

(21) Appl. No.: 16/372,273

(22) Filed: Apr. 1, 2019

(65) Prior Publication Data
US 2019/0228851 A1    Jul. 25, 2019

Related U.S. Application Data

(63) Continuation-in-part of application No. 15/893,573, filed on Feb. 9, 2018, now Pat. No. 10,245,216.
(Continued)

(51) Int. Cl.
*G16H 20/13*    (2018.01)
*A61J 1/14*    (2006.01)
(Continued)

(52) U.S. Cl.
CPC ............... *G16H 20/13* (2018.01); *A61J 1/03* (2013.01); *A61J 1/1412* (2013.01); *A61J 7/0481* (2013.01);
(Continued)

(58) Field of Classification Search
CPC .... A61J 7/0481; A61J 7/0418; A61J 2200/30; A61J 7/049; A61J 7/0076; A61J 1/03;
(Continued)

(56) References Cited

U.S. PATENT DOCUMENTS

| 5,751,661 A | 5/1998 | Walters |
| 6,789,497 B1 | 9/2004 | Aiken |
| (Continued) | | |

*Primary Examiner* — John A Tweel, Jr.
(74) *Attorney, Agent, or Firm* — Chad Peterson

(57) ABSTRACT

Methods, systems and apparatuses, including computer programs encoded on computer storage media, are provided for assisting users with adherence to a medication regimen. An attachable device includes a sensor module releasably attached to an adapter, which is in turn attached to a medication container using a connector. The sensor module can be removed from the adapter to change an included battery without removing the adapter from the medication container. The sensor module is in communication with a user device, such as a smart phone. A user can use an app on the user device to create a medicine regimen, or schedule, and send the schedule to the sensor module. The user can also set notification preferences on the user device to be sent to the sensor module. The sensor module includes audio and/or visual transducers that notify the user to take the medication at the scheduled times. The sensor module further includes one or more buttons that are pressed when a user opens the medication container. The button(s) are configured so the action of the user required to open the container also presses at least one button. The sensor module records the actions of the user, including when the medication container is opened, when a dose of the medication is missed, and when the user presses a mood indication button. The user actions can be transmitted to the user device, which can then transmit the recorded actions to a server. The sensor module may be configured to attempt communication with the user device on a periodic basis to conserve battery life.

9 Claims, 9 Drawing Sheets

Related U.S. Application Data

(60) Provisional application No. 62/457,631, filed on Feb. 10, 2017.

(51) Int. Cl.
*A61J 7/04* (2006.01)
*A61J 1/03* (2006.01)
*G06F 9/54* (2006.01)
*G16H 40/63* (2018.01)

(52) U.S. Cl.
CPC .............. *G06F 9/542* (2013.01); *G16H 40/63* (2018.01); *A61J 2200/30* (2013.01); *A61J 2205/70* (2013.01)

(58) Field of Classification Search
CPC ....... A61J 1/1412; G08B 21/24; G16H 20/13; G16H 40/63; G06F 9/542
USPC ....................................................... 340/686.1
See application file for complete search history.

(56) References Cited

U.S. PATENT DOCUMENTS

| | | | |
|---|---|---|---|
| 8,279,076 B2 | 10/2012 | Johnson | |
| 8,284,068 B2 | 10/2012 | Johnson | |
| 8,727,180 B2 | 5/2014 | Zonana et al. | |
| 8,754,769 B2 | 6/2014 | Stein et al. | |
| 9,125,798 B2 | 9/2015 | Stein et al. | |
| 9,358,183 B2 | 6/2016 | Stein et al. | |
| 9,387,154 B2 | 7/2016 | Aggarwal et al. | |
| 9,507,916 B2 | 11/2016 | Charanis et al. | |
| 9,728,068 B2 | 8/2017 | Engelhard et al. | |
| 10,245,216 B2 * | 4/2019 | Rawal | A61J 7/049 |
| 2001/0028308 A1 | 10/2001 | De Le Huerga | |
| 2012/0160716 A1 | 6/2012 | Chan et al. | |
| 2013/0222135 A1 | 8/2013 | Stein et al. | |
| 2016/0048657 A1 | 2/2016 | LeBrun et al. | |
| 2016/0212389 A1 | 7/2016 | Mehrotra et al. | |

* cited by examiner

SYSTEMS, METHODS, AND APPARATUSES FOR MANAGING ADHERENCE TO A REGIMEN

CROSS-REFERENCE TO RELATED APPLICATIONS

The present application is a continuation-in-part of U.S. patent application Ser. No. 15/893,573, titled "SYSTEMS, METHODS, AND APPARATUSES FOR MANAGING ADHERENCE TO A REGIMEN," filed Feb. 9, 2018, and claims benefit of U.S. provisional patent application Ser. No. 62/457,631, titled "Systems, Methods and Apparatuses for Detecting Opening of Containers," filed Feb. 10, 2017, each of which is incorporated by reference herein in its entirety.

BACKGROUND

This specification relates generally to systems, methods and apparatuses for assisting with adherence to a health or medical routine or regimen, in which a patient or user must open a container, such as a pill bottle, at specified times. Some of the present embodiments also relate generally to a system and method for determining when such a container has been opened, and for providing reminders to a user to assist in adherence to a health or medical routine or regimen.

It is estimated that half of all patients do not take their medications as prescribed. Approximately 125,000 Americans die each year as a result of this non-adherence. Simple forgetfulness is a primary factor for patients not taking their medication. In addition, the same forgetfulness prevents people from adherence to other health and wellness regimens, such as water or other liquid intake goals and the consistent consumption of vitamins and/or other supplements. To help improve adherence to taking medications, there exist specially configured medication containers and/or replacement lids for medication containers. Such devices may remind patients when it is time to take a dose of medication and/or may automatically dispense a proper dose. However, none of these medication containers and/or replacement lids can be applied to (e.g., removably or permanently adhered to) one or more conventional pill containers.

U.S. Pat. No. 8,754,769 to Stein et al. discloses a medication container that senses the opening and/or closing of a cap thereof. The medication container also senses a quantity of medication in the container. However, this patent does not disclose a sensor attachable to an existing medication container that detects the opening thereof. U.S. Pat. No. 9,125,798 to Stein et al. and U.S. Pat. No. 9,358,183 to Stein et al. contain similar disclosures.

U.S. Pat. No. 8,727,180 to Zonana et al. discloses a medication container cap for use with a medication container that controls the dispensing of the medication. The cap includes a door and a ramp for dispensing the medication. However, this patent does not disclose a sensor attachable to an existing medication container that detects the opening thereof.

U.S. Pat. No. 9,507,916 to Charanis et al. discloses a medication container with a lockable lid and a dispensing device that automatically dispenses an appropriate dose of medication at scheduled times. It also includes an internal scale to measure the quantity of medication remaining within the container. This patent also fails to disclose a sensor attachable to an existing medication container that detects the opening thereof.

Therefore, there is a need for systems and methods for improving patient adherence to medication regimens or schedules and other health and wellness regimens which overcomes the preceding disadvantages.

SUMMARY

In accordance with the foregoing objectives and others, methods, systems, and apparatuses are disclosed herein that allow for assisting with adherence to a health or medical routine or regimen, in which a user must open a container, such as a pill bottle, inhaler, pill box, bottle with water or another drinkable liquid, or fluid medicine container at specified times.

In one embodiment, a device is provided that can be attached (e.g., permanently or removably adhered) to a conventional container with a lid, e.g., a pill bottle, and can detect when the container has been opened. The container can be any type of container, e.g., a medication or pill bottle, a liquid bottle, or a bottle containing vitamins or other nutritional supplements.

One or more notifications may be provided to a user when a medication or supplement dose, or another scheduled action, such as fluid intake, is due. Additionally or alternatively, one or more notifications may be provided to a user or a user's medical provider when the user has taken the scheduled dose, or when the user has missed the scheduled dose. Moreover, one or more notifications may be provided to a user and/or the user's medical provider relating to the user's level of compliance with the medication, supplement, or other health or wellness regimen. Scheduled doses and/or notifications relating thereto may be set by a user and/or by a medical provider associated with the user via one or more software applications.

In another embodiment, a system and method for detecting the opening of a container and reporting adherence to a regimen is provided. An attachable device may be attached to a container, such as a pill bottle. The attachable device detects when the container is opened, and sends a message to a user device. The user device records this in a log, indicating that the user has taken a dose of the medication contained in the container at the time the container was opened. Thus, adherence to a medication regimen may be tracked using this system.

The system may be configured to notify the user when the user is scheduled to take the next dose of medication according to the regimen. This notification may be in the form of a sound and/or light alert from the attachable device. In addition, a message may be sent to a device proximate the user, such as a watch or cell phone.

In some embodiments, the attachable device may include one or more buttons or be otherwise configured to enable a user to indicate a general state of being or mood, e.g., feeling good, feeling bad, etc. These indications may be stored on the attachable device, along with other user activities.

Information regarding user activities, e.g., when the medication container is opened, when the user has missed a medication dose, how a user is feeling at specific times, etc., is stored in the attachable device. The attachable device attempts to send the activity information to the user device at specific times. These times may be predetermined, or the attachable device may determine a time to attempt to send the information based on a smart algorithm. The user device may upload the activity information to a server for further analysis, processing, and/or distribution to third parties and/or providers.

One embodiment comprises a device that removably attaches to a medication container, the device comprising: a housing; a transducer for notifying a user; one or more container opening detectors configured to detect when the medication container is opened; a processor; a memory configured to store medication information; a communication module; and a connector for attaching the device to the container.

Implementations of this embodiment may include the one or more container opening detectors comprising one or more detection buttons; the one or more detection buttons being configured to be pressed in the same motion performed to open the medication container; the device comprising three detection buttons; at least one of the one or more detection buttons being disposed at the top of the housing; the detection buttons protruding from a top of the housing by between about 0.70 mm and about 1.15 mm; the device being configured to be removably attached to the lid of the medication container; the housing comprising a diameter of between about 30 mm and about 35 mm; the connector comprising pressure sensitive adhesive tape; the memory further storing activity information; the communication module being configured to send the stored activity information to a user device at a calculated time, wherein the calculated time is determined based on a parameter selected from the group consisting of a user sleep schedule, a user medication schedule, and a time of at least one prior successful transmission of information from the attachable device to the user device; the memory being further configured to store notification information; the device further comprising a power source compartment cover configured to removably attach to the housing and an adapter, the adapter configured to removably attach to the housing such that the adapter substantially covers the power source compartment cover, and wherein the connector is configured to attach the adapter to the container.

Another embodiment comprises a device removably attachable to a medication container comprising a processor and a memory storing instructions that when executed by the processor causes the processor to perform operations comprising: receiving medication information and notification information from a user device, the medication information comprising a time for taking the medication; notifying a user at the time for taking the medication; receiving a signal indicating the user has opened the medication container; storing a dosage time indicating the time the medication container was opened; calculating a transmission time to send the stored dosage time to the user device, the calculation based on at least one prior successful transmission of information from the attachable device to the user device; and sending the stored dosage time to the user device at the calculated transmission time.

Implementation of this embodiment may include one or more of the following: the device is attachable to the lid of the medication container; the device comprises a detection button, and further wherein the signal indicating the user has opened the medication container is based on the user having pressed the detection button; the detection button is configured to be pressed in the same motion performed to open the medication container; the device comprises three detection buttons; the calculation of the transmission time is further based on a medication schedule of the user; the calculation of the transmission time is further based on a sleep schedule of the user; the operations further comprise notifying the user that the container has been opened.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

Figure 1:
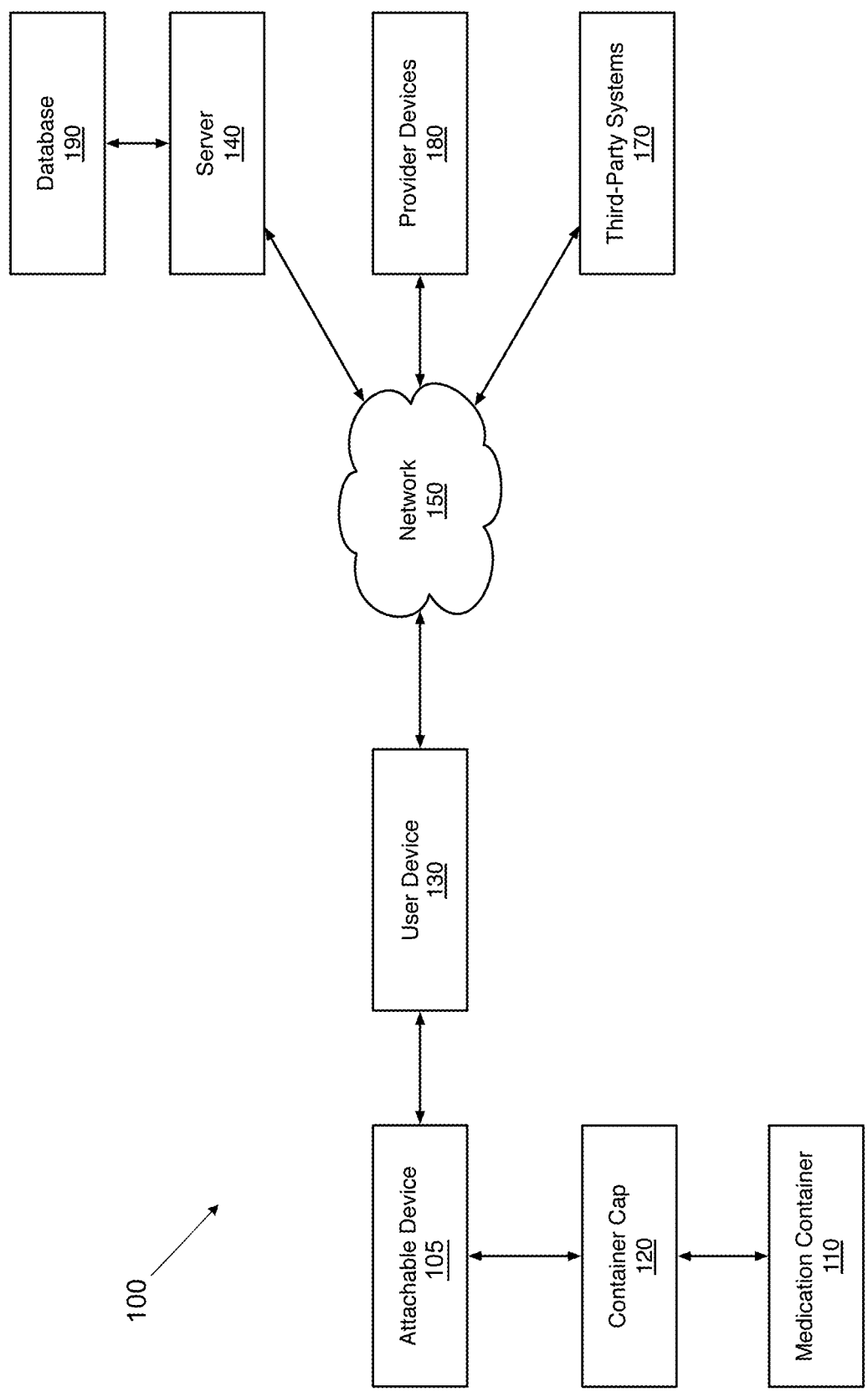
FIG. 1 shows one embodiment of a system according to the principles of the present disclosure.

Various methods, systems and apparatuses are discussed herein that assist users with adherence to a health or medical routine or regimen, in which the user must open a container, such as a pill bottle, at specified times (e.g., to take medication contained within the container). The described embodiments allow for the notification of users to, e.g., take their medication, at specified times, the collection of information relating to the user's adherence to a predetermined health and/or medical routine, and/or the reporting of such information to the user and/or a medical provider associated with the user.

As used herein, "medication information" includes, but is not limited to: the name of the person taking the medication; the name of the medication; medication strength; the type of medication container (e.g., pill bottle, medicine box, asthma inhaler, etc.); name, address, and contact information (e.g., phone number) of the prescribing physician; name, address, and contact information (e.g., phone number) of the dispensing pharmacy; medication schedule, including, e.g., dose frequency (e.g., daily, every other day, weekly, etc.), the number of doses per day, times of the doses, number of pills to take for each dose, number of doses remaining, number of days the schedule is to be followed, information regarding the attachable device associated with the medication (e.g., MAC address, unique device ID, etc.), etc. Medication information may also include a setting for how to handle a missed dose (e.g., take the missed dose at the next scheduled dose, skip the dose, etc.).

As used herein, "notification preferences" and "notification information" include, but are not limited to: type of notification (e.g., audio, visual, etc.), the volume of an audio notification (including mute, or no sound), the number of times the audio notification sounds, the frequency of the audio notification (if the audio notification is a single tone or series of tones), a multi-note audio notification selection, the brightness and/or color of a visual notification, the number of times the visual notification repeats (e.g., the number of flashes if the visual notification is an LED), the number of separate notification windows, the time between notification windows, text message to send (to, e.g., the user device), phone number for text messages, push notification timings (for user devices) and content, etc.

"Notification preferences" and "notification information" also include the activity indicated by the notification, e.g., notification instructing the user to take a dose, notification that a dose was missed, notification that a dose was taken, etc.

In addition, "notification preferences" and "notification information" may include a window of time prior to the scheduled dose during which the user may take the dose without the notification sounding at the scheduled time of the dose. For example, if a dose of medication is scheduled for 8:00 am, and the before dosage window (as this setting may be called) is set for 15 min, the user may take the dose between 7:45 am and 8:00 am without the notification sounding at 8:00 am.

As used herein, "activity information" includes, but is not limited to: type of activity, e.g., medication dose taken (also referred to herein as a dosing event), medication dose missed, etc.; and time and date of the activity.

As used herein, "user information" includes, but is not limited to: user identification information (e.g., name, age, date of birth, sex, social security number, unique ID, photo, etc.); contact information (e.g., email address, physical address, phone number, etc.); billing information (e.g., credit card information, billing address, etc.); medication information; user vitals information (e.g., weight, height, blood pressure, blood sugar, pulse, cholesterol levels, etc.); user mood information; and/or activity information. User information may also include information relating to one or more attachable devices associated with the user (e.g., MAC address, unique device ID, etc.); medication information; notification preferences; and/or information relating to third-parties associated with the user (e.g., the prescribing doctor or health care provider, the pharmacy dispensing the medication, an attending or other health care provider who may be sent notifications).

Referring to FIG. 1, an exemplary system 100 is presented. As shown, the system comprises an attachable device 105 attached to a lid, cap, or top 120 of a container 110, such as a pill bottle. The attachable device 105 is in communication with a user device 130, via a wireless connection, e.g., a Bluetooth Low Energy (BLE) connection. The user device may comprise any device capable of performing the functions described herein, e.g., a smart phone, table, smart watch, pager, personal digital assistants (PDAs), personal computer, etc. While one attachable device 105 is shown, multiple attachable devices may be in communication with the user device.

The attachable device(s) 105 are adapted to detect certain activities, such as when the container 110 is opened (e.g., when buttons on the cap 120 are pressed in the process of removing the cap from the container) and/or when a dose of medication is missed (e.g., when the cap is not removed when a dose is due). When a device detects such an activity, information regarding the activity is stored in the device and/or transmitted to the user device 130. The timing of the transmission may be synchronized with the user device as described in more detail below.

The attachable device 105 is configured to notify the user when the user is scheduled to take the next dose of medication according to the user's medication regimen. To this end, the attachable device stores information regarding the user's medication regimen and notification preferences.

The notification may be visual (e.g., LED or other light) or aural (e.g., via a speaker or buzzer). Details regarding the notification are based on the user notification preferences, which may be set up via the user device.

If the user takes the medication as prompted, the attachable device 105 stores this activity in internal storage. If the user has not taken the medication within a preset amount of time after the notification, the user may be given another notification based on the user's notification preferences. If the user does not take the medication after the final notification, the missed dose is stored as activity information.

The attachable device may be configured to attempt to send activity information to the user device periodically. The times the attachable device attempts to send information may be configurable at the user device, or may be calculated via an algorithm based on, e.g., prior connection times, etc. At each attempt to connect, the attachable device attempts to detect the user device, and, if the user device is detected, sends the activity information to the user device. If there has been no activity information stored since the last successful transfer, no attempt to connect will be made.

The information regarding the user's medication regimen and notification preferences is also stored in the user device 130. As such, the notifications may originate from the user device, e.g., if the notification is a sound, the sound is generated by an audio source, e.g., a speaker, a buzzer, etc., in the user device. In addition, a notification provided by the user device may be in the form of a push notification or other alert used by smart phones, tablets, smart watches, and/or personal computers.

The system 100 may also comprise a server 140 in communication with a database 190, which stores user information. The user device and the server may be in communication via a network 150 (e.g., Internet, LAN, cellular, intranet, etc.).

The server 140 is adapted to receive, determine, record and/or transmit user information for any number of users. Such information may be manually entered or selected by a user via an online, mobile, or desktop application running on the user device 130 and/or a provider device 180. The server may store received or determined information in the database 190.

The user device 130 is adapted to transmit activity information received from the attachable device to the server 140 via the network 150. The user device may be further adapted to receive medication information and/or notification information from the server 140 via the network 150 and transmit the received medication information and/or notification information to the attachable device 105.

Optionally, the server 140 may be connected to one or more third party systems 170 via the network 150. Third party systems may store information in one or more databases that may be accessed by the server. Third party systems may include, but are not limited to: electronic medical record systems; other healthcare provider systems; calendaring and/or scheduling systems; backup systems; communication systems and/or others.

The server may be capable of retrieving and/or storing information from third party systems 170, with or without user interaction. Moreover, the server may be capable of communicating stored information to third party systems, and may notify users of such communications.

Optionally, the system may include one or more provider devices 180. The provider devices allow health providers or other parties to create, access, update and/or delete user information stored in the database 190, e.g., via a client application running on a provider device.

While the above description focuses on the case where the container 110 is a pill bottle, the container may be any type of container, for example, a pill bottle, a pill box, an inhaler (for, e.g., asthma medication), a bottle with water or another drinkable liquid, a liquid medicine, or a bottle containing nutritional supplements, etc. In the case where the container is a water bottle, the system may remind the user to drink a certain amount of water, and the attachable device may log the user's intake of water. In the case where the container holds vitamin or nutritional supplements, the system may remind the user that it is time to take the next dose of the vitamin or nutritional supplement, and the server 140 may log the user's adherence to a supplement schedule.

In one embodiment, the system may use the information regarding the user's vitals, mood, etc., to calculate or otherwise determine the effectiveness of the medication. User vitals information and mood information may be manually input by the user at either the attachable device or the user device. In addition or alternatively, user vitals information may be retrieved from connected devices (not shown), e.g., blood pressure monitors, activity monitors (e.g., Fitbit), etc., and/or apps on the user device, e.g., fitness tracking apps (e.g., Google Fit), etc. Connected devices may communicate information directly to the user device and/or attachable device, or may communication information through network 150.

Figure 2:
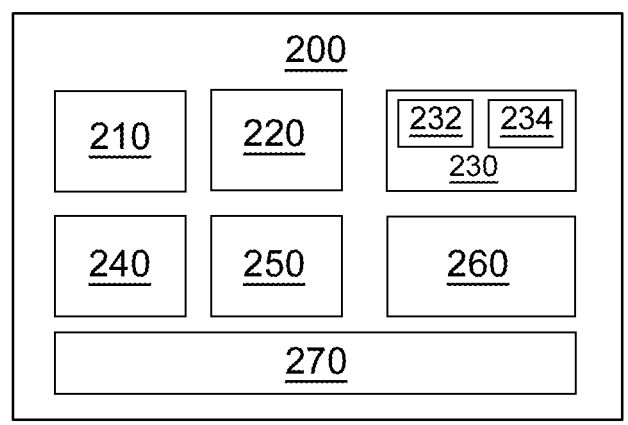
FIG. 2 shows an embodiment of an attachable device according to the principles of the present disclosure.

Referring to FIG. 2, a block diagram of an exemplary attachable device 200 is illustrated. The device 200 comprises a communications module 210, a detection module 220, an optional reminder module 230 (optionally comprising one or more audio transducers 232 (e.g., speakers, buzzers, etc.) and/or visual transducers 234 (e.g., LEDs, etc.)), a processor 240, a power source 250, and memory 260. The device 200 also comprises a connector 270 for securing the device to a top or lid of a container. The attachable device further comprises a device ID, such as a MAC address or other unique ID, which may be employed to distinguish the device from any other devices that may also communicate with the user device.

The attachable device 200 is sized to be able to unobtrusively attach to the lid or cap of a container, such as a pill bottle, a bottle with water or another drinkable liquid, or a bottle containing nutritional and/or other types of supplements.

The connector 270 is configured to attach the device 200 to the container. The connector may comprise a sticky substance, allowing the device 200 to stick to the lid of the pill bottle, water bottle, etc. In one embodiment, the connector comprises double-sided tape, e.g., pressure sensitive adhesive (PSA) tape. Alternatively, the connector may comprise a magnet, with a corresponding ferromagnetic material formed in or attached to the lid of the container.

The attachable device further comprises a processor 240, such as a general purpose microprocessor, special purpose microprocessor, and/or any other kind of central processing unit ("CPU"). The attachable device also comprises memory 260 in communication with the processor, communications module 210, detection module 220, and/or reminder module 230, such as but not limited to, ROM (e.g., NAND flash, NOR flash, flash on another processor, other solid-state storage, mechanical or optical disks) and/or RAM. The memory may store any of the information described herein, such as but not limited to activity information, notification information, and/or medication information. Flash memory lends itself to applications such as the present in that it has good shock resistant characteristics and may retain stored data without the need for an active power source.

The memory may store executable code or instructions for one or more applications. When an application is requested to be executed, the processor retrieves corresponding executable code and/or data from the memory and executes it. The executable code can be temporarily or permanently stored on the memory or storage of the application processor.

The communication module 210 may comprise a wireless communications circuit, such as BLE, NFC, RFID, ZIG-BEE, WiFi, or cellular link (e.g., CDMA or GSM). The communication module may be employed to send and/or receive real-time or stored information, such as activity information and/or notification information to/from the user device 130 via BLE or other communications protocols.

The detection module 220 may comprise a sensor or other device that detects when the lid or cap of the medication container is removed. The sensor may comprise one or more buttons that are pushed when the user takes the medication. The button(s) may be pushed in conjunction with the removal of the lid, i.e., the push motion required to remove the lid also pushes the button(s). Alternatively, the user may be required to push a button in a separate motion. As an additional alternative, a motion sensor, e.g., an accelerometer or a gyroscope, may be configured to detect the "push and twist" motion necessary to remove the lid.

The reminder module 230 is configured to remind the user to take the required medication or to perform other required tasks at the scheduled times. The reminder can be in the form of an audio notification (e.g., a sound or music generated by a speaker or buzzer 232) or a visual notification (e.g., a flashing or non-flashing light, such as a LED light 234). The number of notifications, type of notification(s), timing of the notification(s), and other notification preferences may be specified by the user and/or the user's provider, and may be configurable at the user device, the provider device, or the server.

The device may comprise one or more power sources 250 that can be utilized to power the electrical components thereof. In certain embodiments, the attachable device may comprise a removable and/or rechargeable power source, such as a rechargeable battery.

The attachable device is configured to store activity information in memory 260 when certain events happen. For example, when the detection module 220 detects that the lid of the medication container has been removed, the time and date of the opening of the container is stored. In addition, if the container remains unopened a configurable (based on entered medication information) amount of time after the final notification to take a medication dose, the time and date of the missed dose is stored.

The attachable device periodically sends stored activity information to the user device. In one embodiment, the attachable device and the user device may be configured with a smart algorithm to coordinate communication of activity data from the attachable device to the user device in order to preserve the life of the power source (e.g., battery) of the attachable device.

The communication algorithm on the attachable device attempts periodic connections to the user device. The timing of the connection attempts may be configurable on the user device, or may be determined based on an algorithm stored in the memory of the attachable device. If the user device is detected, the attachable device sends all activity data to the user device. After the activity data is sent, the user device may send information and preferences (e.g., medication information, notification settings, etc.) updates to the attachable device. The user device may also send algorithm configuration parameters to the attachable device to update the timing algorithm.

The timing algorithm uses data including user medicine schedules, user sleep schedule, and past connection times to compute the times and time ranges that have the highest probability of the user device being in proximity to the attachable device. The user medicine schedules may be retrieved from medication information stored on the attachable device. The user sleep schedule may be input by the user, or may be retrieved from the user device. In one embodiment, the timing algorithm gives times the user is scheduled to take medication and past connection times a higher probability of a successful connection, and user sleep times a lower probability. The algorithm then attempts connection with the user device at the times or time ranges with the highest probability. The attachable device may attempt communication with the user device a predetermined number of times per day (when there is activity data to send). In one embodiment, the attachable device attempts communication between 4 and 10 times per day.

Figure 3:
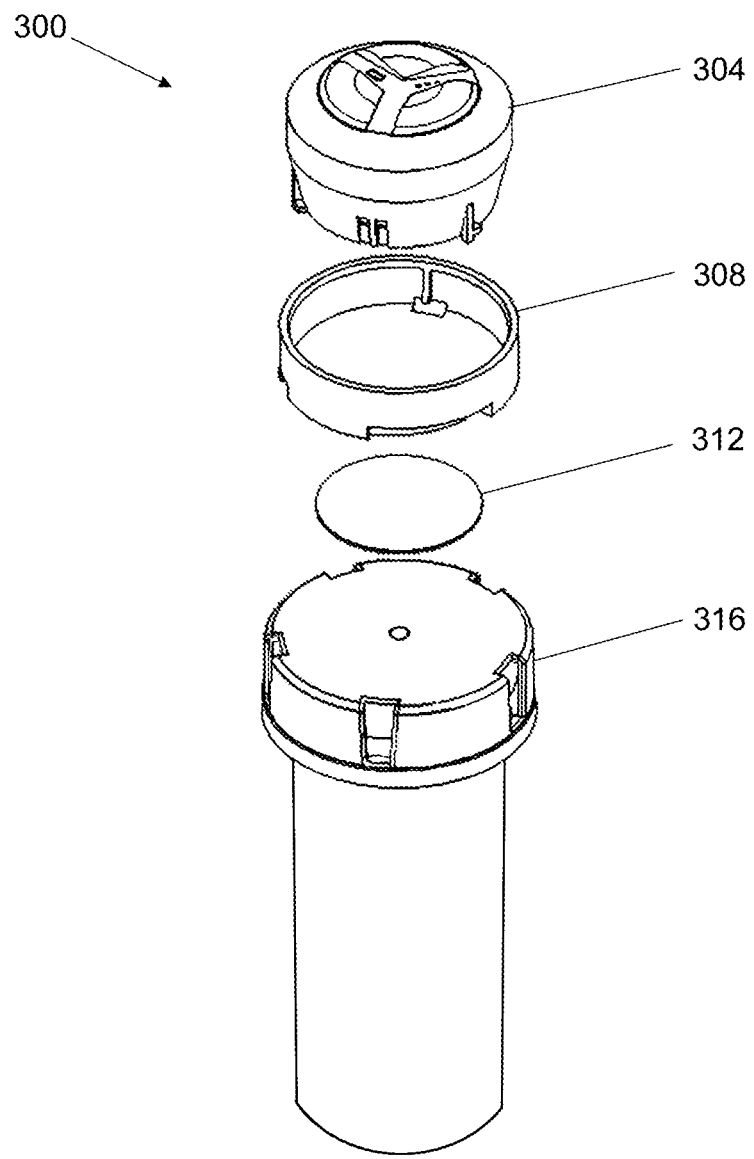
FIG. 3 shows an embodiment of an attachable device, illustrating attachment to a medicine container.
Figure 4:
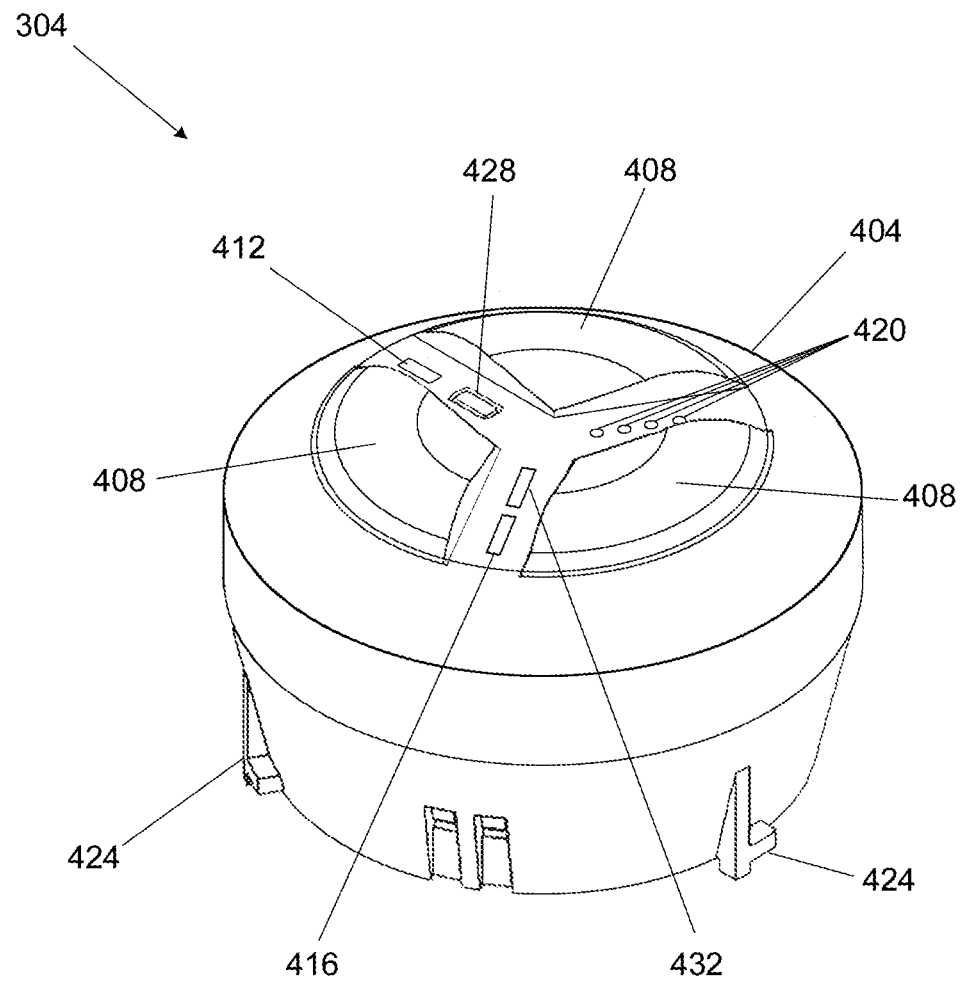
FIG. 4 shows one embodiment of a sensor module according to the principles of the present disclosure.
Figure 5:
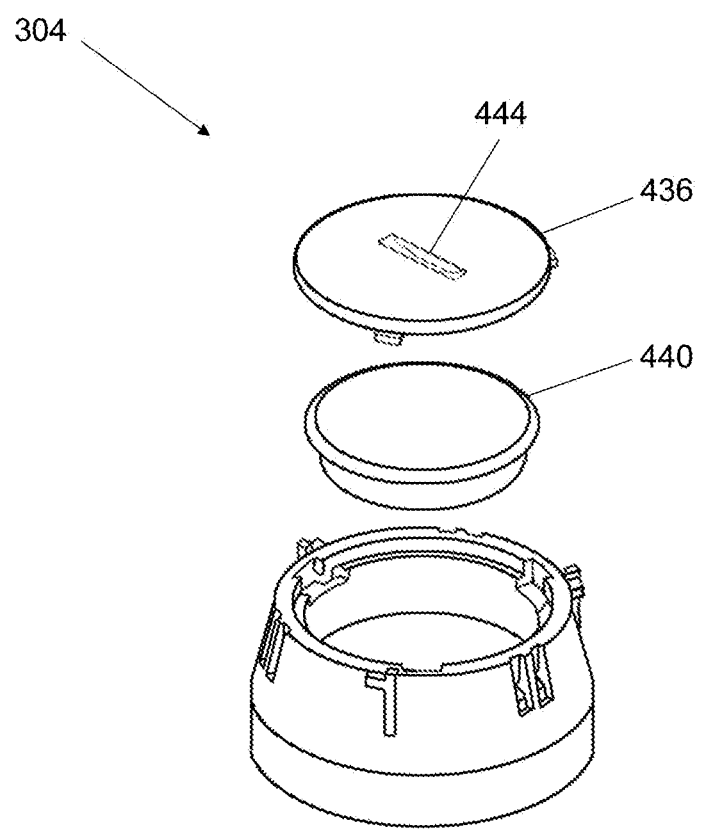
FIG. 5 shows a partially exploded view of a sensor module.

One embodiment of the attachable device is illustrated in FIGS. 3-5. As shown in FIG. 3, the attachable device 300 comprises a sensor module 304, an adaptor 308, and a connector 312. The sensor module attaches to the adaptor using locking structure(s) 424. The locking structures enable the sensor module to be easily locked in place with respect to the adaptor, but also easily removed, enabling access to the battery compartment (as shown in FIG. 5). The adaptor attaches to the pill bottle 316 using the connector. In one embodiment, the adhesive comprises double-sided tape, e.g., pressure sensitive adhesive (PSA) tape.

The attachable device is sized to fit unobtrusively on the medicine container to which it is attached, so as to not interfere with the opening and closing process. It will be appreciated by one of ordinary skill in the art that the attachable device may be manufactured in various sizes to fit the different sizes of medication container lids. Common diameters of medication container lids include 27 mm, 35 mm, and 42 mm.

In one embodiment, the sensor module has a diameter of between about 30 mm and about 35 mm, and a height of between about 18 mm and 23 mm. In this embodiment, the adaptor has a diameter of between about 32 mm and about 36 mm, and a height of between about 8.5 mm and about 10 mm. The PSA tape has a diameter of between about 21 mm and about 27 mm, and a height of between about 0.3 mm and about 0.7 mm.

In an alternative embodiment, sized to fit smaller medicine container lids, the sensor module has a diameter of between about 23 mm and about 27 mm, and a height of between about 18 mm and 23 mm. In this embodiment, the adaptor has a diameter of between about 24 mm and about 27 mm, and a height of between about 8.5 mm and about 10 mm. In this embodiment, the PSA tape has a diameter of between about 19 mm and about 23 mm, and a height of between about 0.3 mm and about 0.7 mm.

As shown in FIG. 4, the sensor module 304 includes a housing 404, one or more detection buttons 408, one or more visual indicators 412, an update button 416, a connect button 428, a diagnostic button 432, one or more audio ports 420, one or more audio indicators, e.g., speakers, buzzers, etc. (not shown), and one or more locking structures 424.

The housing 404 may be comprised of any suitable material, e.g., plastic, polyethylene, polypropylene, polyethylene terephthalate, a thermoplastic (e.g., acrylonitrile butadiene styrene (ABS)), silicon, etc. The housing encloses and protects the internal components of the sensor module, including any required internal components of the communications module 210, detection module 220, reminder module 230, processor 240, power source 250, and memory 260.

The detection buttons 408 are configured so they are pushed as a consequence of a user opening the pill bottle. In general, pill bottles may be configured with "childproof" caps, requiring the user to push down on the cap before the cap is rotated and able to be removed. As the user pushes down on the cap, one or more of the detection buttons will be pressed without the user having to perform another action. Any of the buttons being pressed is interpreted by the sensor module 304 as a medication dosing event. In an alternative embodiment, the button must be pressed for at least a short interval, e.g., 0.25 seconds, for the button press to be interpreted as a dosing event. In another alternative embodiment, more than one button must be pressed at the same time for the button press to be interpreted as a dosing event.

In one embodiment, the sensor module comprises three detection buttons evenly spaced around the top of the housing. In one embodiment, the detection buttons protrude from the top of the housing by between about 0.70 mm and about 1.15 mm.

The visual indicators 412 may comprise one or more light sources, e.g., LEDs. The visual indicators may light to indicate one or more notifications or statuses, e.g., that it is time for the user to take the medication, an error mode, that a dosing event has been recorded, Bluetooth advertising on, connection made to user device, etc. The visual indicators may flash or blink one or more times to provide the desired notification or indicate the desired status, and the number of flashes or blinks may be user configurable at the user device. The visual indicators may comprise one or more colors of lights, and the combination of, or alternation of, different colors of light may indicate a particular notification or status. For example, a blinking red light may indicate a notification for the user to take the medication, while a blinking green light may indicate a successful dosing event.

The audio ports 420 allow sound from the one or more audio indicators to reach the user more effectively. The audio indicators may comprise one or more speakers, buzzers, or other audio output devices or transducers. The audio indicators may make a particular sound or play a piece of music to indicate one or more notifications or statuses, e.g., that it is time for the user to take the medication, an error mode, that a dosing event has been recorded, etc. For example, the audio indicator may beep several times to indicate a notification for the user to take the medication, while a chime may indicate a successful dosing event.

The update button 416, when pressed, enables an over-the-air (OTA) update of the attachable device for updating, e.g., firmware.

The connect button 428, when pressed, causes the communication module to attempt to connect with the user device and transmit activity information as described herein, enabling a sync with the user device at any time. This may be configured to happen only after a long press (e.g., 5-10 secs) to prevent accidental presses while opening the medication container from attempting a sync operation.

The connect button is also be configured to wirelessly advertise the attachable device (e.g., Bluetooth advertising) when pressed, to enable connection with the user device.

When the diagnostic button 432 is pressed, the attachable device enters a diagnostic mode, allowing the user to troubleshoot problems. The diagnostic button may require a long press, e.g., 25 seconds, to cause the attachable device to enter diagnostic mode.

The reset button (not shown) may be configured to reset the attachable device to factory settings, enabling the device to be used on a different medication container.

The reset button, connect button, update button, and diagnostic button may be configured such that normal opening and closing of the medication container is unlikely to cause them to be pressed or otherwise activated. For example, the connect, update, and diagnostic buttons may be recessed below the surface of the housing 404, and the reset button may be disposed inside the housing. Other configurations will be readily apparent to one of ordinary skill in the art.

The locking structure(s) 424 comprise one or more connectors that are formed in the housing 404. The connector(s) match corresponding connector(s) on the adapter to enable the sensor module to be easily attached to and removed from the adapter. For example, a locking structure may comprise one or more protrusions that match one or more holes or grooves on the interior surface of the adapter. The connector(s) may be configured such that a user may insert the sensor module into the adaptor, then rotate the sensor module to lock it into place.

The internal circuitry of the sensor module may be configured on one or more circuit boards comprising a substrate and conductive traces, tracks, and/or pads, e.g. printed circuit boards (PCB). The components are configured on the circuit boards to keep any radio frequency (RF) antennas substantially free from interference, and to place audio and visual indicators (e.g., speakers, buzzers, LEDs) near the top of the sensor module.

Referring to FIG. 5, the sensor module 304 includes a battery compartment cover 436, enabling access to a battery 440. The battery compartment cover may include a slot 444, enabling removal of the cover from the sensor module via a twisting action using a flat object, e.g., a coin. This configuration enables the user to detach the sensor module from the adapter and remove the battery compartment lid from the sensor module to gain access to the battery for replacement, with the adapter remaining attached to the medication container.

Figure 6:
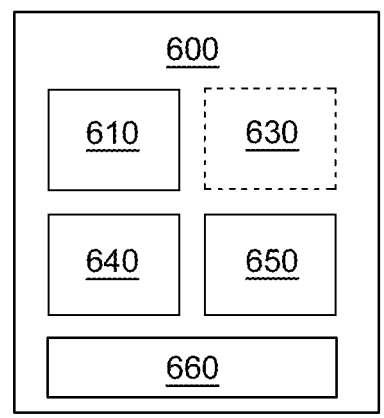
FIG. 6 shows one embodiment of a user device according to the principles of the present disclosure.

Referring to FIG. 6, a block diagram of an exemplary user device 600 is illustrated. The user device may comprise any device capable of carrying out the required functions, e.g., a smart phone, tablet, smart watch, person digital assistant (PDA), personal computer, etc.

As shown, the user device 600 comprises a communications module 610, an optional reminder module 630, a processor 640, a power source 650, and a memory 660.

The communication module 610 enables communication with the attachable device 105 and the server 140. The communication module comprises a wireless communications circuit, such as BLE, NFC, RFID, ZIGBEE, WiFi, or cellular link (e.g., CDMA or GSM). The communication module is employed to send and/or receive real-time or stored information to and/or from the attachable device 105 (e.g., via BLE or other communications protocols).

In one embodiment, the attachable device 105 and the user device may be configured with a smart algorithm, as further described herein, to coordinate communication of activity data from the attachable device to the user device in order to preserve the life of the power source of the attachable device.

The communication module may also be employed to send collected activity information to the server 140 (e.g., via WiFi or cellular) for logging and analytics.

The optional reminder module 630 may be configured to remind the user to take the required medication or to perform other required tasks at the scheduled times. The reminder can be in the form of an audio notification on the user device (e.g., a sound or music), or a visual notification (e.g., a popup window, a push message, text (SMS) message, email, or other message). The user device and attachable device may be configured so notification may occur on both devices.

The processor 640, power source 650 and memory 660 may be implemented in similar manner as that described above with respect to the attachable device.

The user device further comprises an application, through which the user may enter, update, and/or view user information, including medication information and notification preferences. Through the application, the user may also view activity information associated with one or more attachable devices in communication with the user device. This application may be in the form of a downloadable application installable and executable on the user device. Additionally or alternatively, the application may be available as a web application, accessible via an internet browser on the user device.

The application may include a sync option to manually cause the attachable device to transmit the information to the user device. When the user selects this option, a list of available attachable devices is shown, and the user selects from among them. The user then presses the connect button 428 on the selected attachable device. A long press, e.g., 5-10 secs, may be required. The devices then connect, and the attachable device sends the activity data to the user device as described herein.

Figure 7:
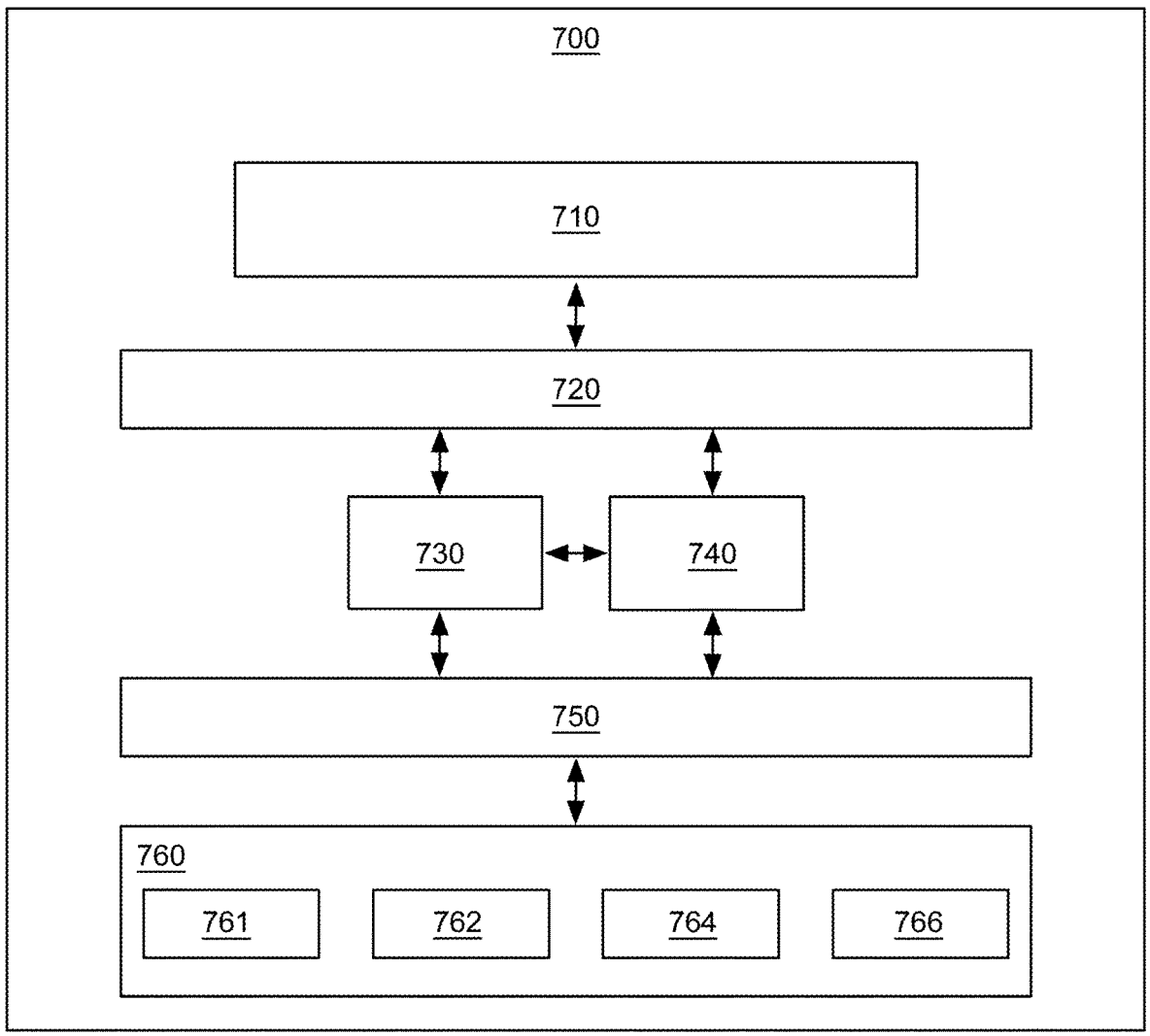
FIG. 7 shows one embodiment of a server according to the principles of the present disclosure.

Referring to FIG. 7, a block diagram of an exemplary server 700 is illustrated. As shown, the server 700 may comprise hardware 760 such as any number of processors 762, RAM 764, and internal or external memory 766. The server may include a network interface 761 such that it may access a network to send or receive information.

As shown, at least one database 710 may be accessed by the server 700. Although shown as internal to the server 700, it will be appreciated that the database may be accessed by the server over a network or via another wired or wireless connection. The server 700 may store desired or required information in the database 710 and may access the same to retrieve the information. The database 710 may include a number of tables adapted to store information relating to users.

The database 710 may be in communication with an object relational mapping ("ORM") 720, also known as an object relational model or object-relational database management system. Although shown as internal to the server 700, it will be appreciated that the ORM may be accessed by the server over the network or via physical connection.

The ORM 720 may be in communication with a Universal Resource Indicator ("URI") mapper 730 and a Rest API generator 740. The URI mapper 730 may map a URI into a pointer to an internal program, view, logic, or presentation of data within the system, based on one or more rules of a matching object specified in a collection of mapping objects. The matching object may be a regular expression. The URI mapper may be in communication with a web server 750.

The Rest API generator 740 may be in communication with a web server 750 as to send and/or receive data to/from client devices (e.g., user device 130, provider device 180)

communicating with the server 700 (e.g., using HTTP and/or HTTPS). The Rest API generator 740 may prepare data stored in the database 710 for delivery to a client device or may prepare data received from a client device for storage in the database 710. The Rest API generator may be capable of translating between formats including, but not limited to JSON, XML and the like. The Rest API generator 740 may be capable of automatically generating URIs based upon data structures observed in the ORM 420 for access by client devices.

A web server 750 may be adapted to deliver web pages on request to users using the Hypertext Transfer Protocol (HTTP and/or HTTPS) or similar protocols. This allows for delivery of HTML documents and any additional content that may be included by a document, such as images, style sheets and scripts.

In one embodiment, a client device (e.g., user device 130, provider device 180) may employ a web browser or similar client application to engage in communication with the web server 750. For example, a client application may make a request for a specific resource using HTTP/HTTPS and the web server may respond with the content of that resource or an error message if unable to do so. The resource may be data or a file stored in a database 710. The web server 750 can receive content from a user, possibly using HTTP/HTTPS.

It will be apparent to one of ordinary skill in the art that, in certain embodiments, any of the functionality of the server may be incorporated into a client, and vice versa. Likewise, any functionality of a client application may be incorporated into a browser-based client, and such embodiments are intended to be fully within the scope of this disclosure. For example, a browser-based client application could be configured for offline work by adding local storage capability, and a native application could be distributed for various native platforms via a software layer that executes the browser-based program on the native platform.

The server 700 may comprise a monitoring application configured to receive activity information and to store the received information in the user's account. The server may keep track of the adherence of the user to the medication regimen, and prepare and/or send reports regarding the user's adherence to the user and/or the user's provider (e.g., via user device 130 and/or provider device 180). In one embodiment, such reports may be in the form of a score, such as a percentage of adherence. For example, the report can indicate that the user was "95% compliant" over the past month or other time period.

In certain embodiments, a user or provider may access the monitoring application running on the server via a user device or provider device. Generally, a user device or provider device may be any device capable of accessing the server, such as by running a client application or other software, like a web browser or web-browser-like application. Exemplary user or provider devices may include general purpose desktop computers, laptop computers, handheld devices, smartphones, and/or tablets.

Each user or provider device may have a client application running thereon, where the client application(s) may be adapted to communicate with the monitoring application running on the server. Such a configuration may allow users of client applications to input user information and/or interact with the monitoring application from any location that allows for access to the server.

Client applications may be adapted to present various user interfaces to users. Such user interfaces may be based on access privileges and/or information sent by the server, and may allow the user to send and receive data. Each client application may comprise HTML data, images, icons, and/or executable code. The executable code may be composed in JavaScript, ECMAscript, coffeescript, python, Ruby or any other programming languages suitable for execution within the client application, or translation into a client application executable form.

The server may be implemented on any system with a processor that is capable of performing the functions described herein, including, but not limited to, server computers, desktop computers, laptop computers, handheld devices, tablet computers, smartphones, etc.

In one embodiment, communication between a client application and a monitoring application running on the server may involve the use of a translation and/or serialization module. A serialization module can convert an object from an in-memory representation to a serialized representation suitable for transmission via HTTP or another transport mechanism. For example, the serialization module may convert data from a native Python, Ruby, or Java in-memory representation into a JSON string for communication over the client-to-server transport protocol. After the JSON string is received by the receiver, a de-serialization module may convert the JSON string back into the native Python, Ruby, or Java in-memory representation for use by the client application or the patient monitoring and management application.

Figure 8:
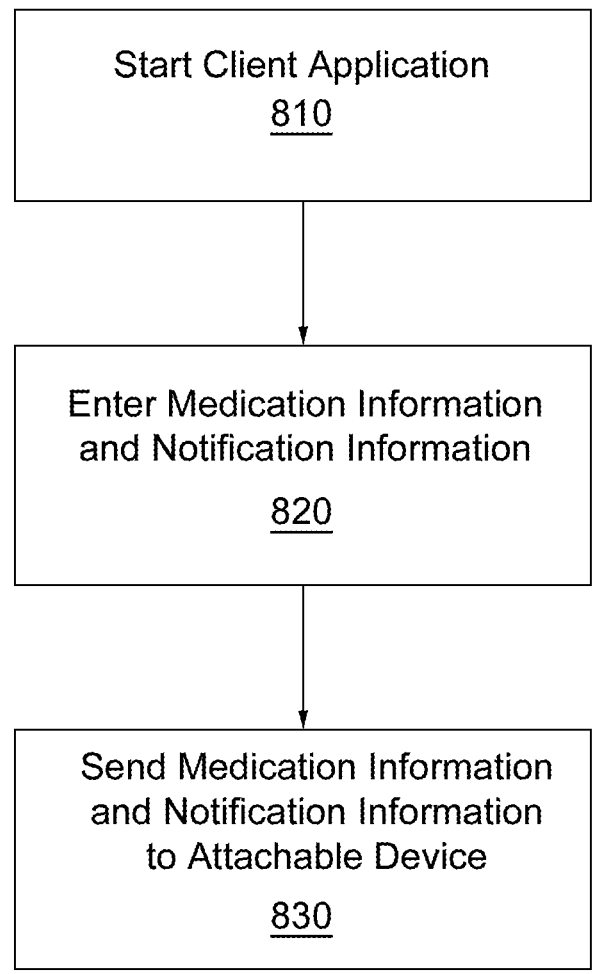
FIG. 8 shows a method for setting up a medication regimen or schedule according to the principles of the present disclosure.

Referring to FIG. 8, a method for creating a medication regimen is illustrated. In step 810, a client application is started on a client device (e.g., a user device 130 or provider device 180). In step 820, medication information (e.g., medication name, schedule, etc.) is entered, optionally with notification information (e.g., types of notifications to prompt the user to take the medication) regarding the regimen. It will be appreciated that notification information may be manually entered or automatically generated by the system based on the medication information.

Entered medication information may include one or more of the following: the name of the medication; medication strength; the type of medication container (e.g., pill bottle, medicine box, asthma inhaler, etc.); name, address, and contact information (e.g., phone number) of the prescribing physician; name, address, and contact information (e.g., phone number) of the dispensing pharmacy; medication schedule, including, e.g., dose frequency (e.g., daily, every other day, weekly, etc.), the number of doses per day, times of the doses, number of pills to take for each dose, number of days the schedule is to be followed, etc. Medication information may also include a setting for how to handle a missed dose (e.g., take the missed dose at the next scheduled does, skip the dose, etc.).

Entered notification information may include one or more of the following: the volume of an audio notification (including mute, or no sound), the number of times the audio notification sounds, the brightness and/or color of a visual notification, the number of LED flashes if the visual notification is an LED, the number of separate notification windows (e.g., times the notification will be presented), the time between notification windows, push notification timings (for user devices) and content, etc.

The entered notification information may also include the type of notification, e.g., notification to take a dose, notification that a dose was missed, notification that a dose was taken, etc.

In addition, notification information may include a window of time prior to the dosage during which the user may take the dose without the notification sounding at the scheduled time of the dose. For example, if a dose of medication is scheduled for 8:00 am, and the before dosage window (as this setting may be called) is set for 15 min, the user may take the dose between 7:45 am and 8:00 am without the notification sounding at 8:00 am.

The user may also input a particular sequence of notifications, e.g., visual notification first, then an audio notification, and finally an SMS notification.

Any of the notification information can be entered and stored on a per-user or per-medication basis.

In step 830, the medication information and notification information is sent to an attachable device. The attachable device is identified by a unique ID, e.g., a MAC address or other ID. As discussed above, the user device and/or the attachable device can then remind the user the take the medication at the scheduled times by notifying the user per the notification settings. The attachable device is configured to operate independently of the user device after it has been configured.

Figure 9:
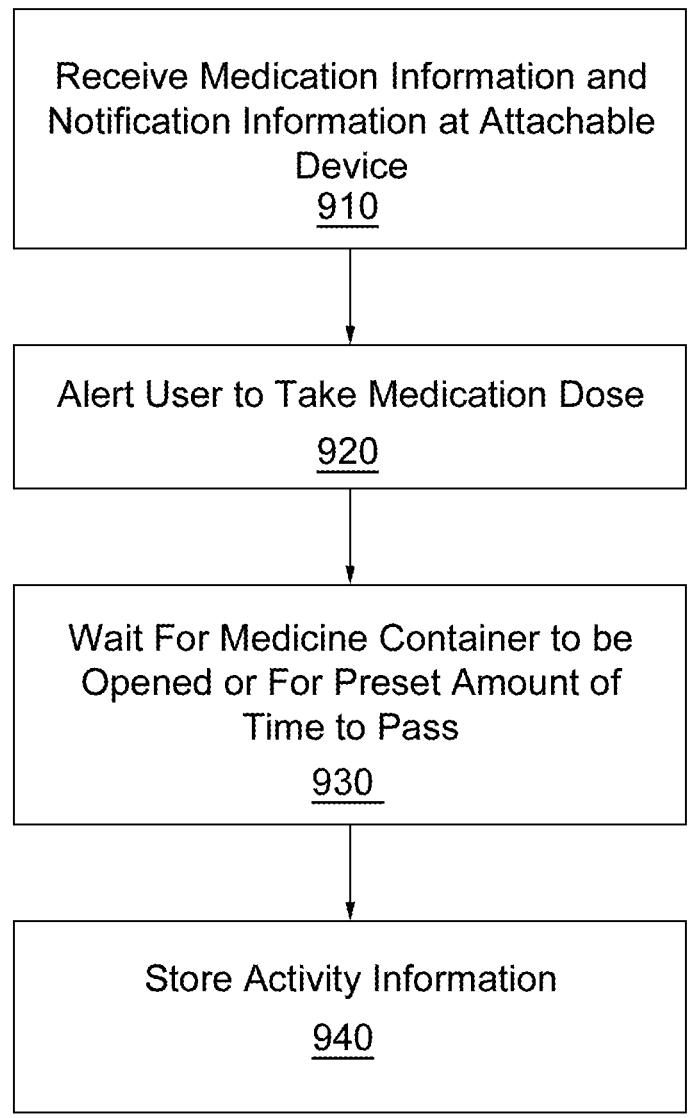
FIG. 9 shows a method for notifying a user and transmitting activity data according to the principles of the present disclosure.

Referring to FIG. 9, a method for reminding a user to take a scheduled dose of medication is illustrated. In step 910, the attachable device receives medication information and notification information. In step 920, the attachable device, at or about the scheduled time of the next dose, notifies the user that it is time to take the next dose. This notification may be, e.g., visual, aural, a push message on the user device, etc., as specified by the notification information.

In step 930, the attachable device waits for a preset amount of time (as indicated by the notification information) for a signal from the detection module that indicates that the medication container has been opened. In the embodiment of FIGS. 3-5, the signal is sent when the user presses one of the detection buttons 408. One or more of the buttons may be automatically pressed, e.g., through the normal push-and-twist motion of opening a medicine bottle, or the user may deliberately press one of the buttons to indicate that a dose was or is being taken. The latter may be useful when the attachable device is attached to a medicine container that is not a traditional pill bottle, e.g., a medicine box.

In step 940, if one of the detection buttons is pressed within the preset amount of time, the attachable device stores activity information identifying that a dose was taken and the time and date that the dose was taken. If one of the detection buttons is not pressed by the expiration of the preset amount of time, the attachable device may notify the user again, depending on the notification settings. If the final notification has been given to the user, the attachable device stores activity information indicating that a dose of medication was missed.

In one embodiment, if one of the detection buttons was pressed, the attachable device and/or the user device determines if the medication needs to be refilled. This may be determined by, e.g., comparing the number of doses remaining to a threshold value. The threshold value may be user-configurable, or may be determined by the system based on, e.g., the number of doses taken per day, how long a medication refill takes to be delivered after it is ordered, etc.

If the number of doses remaining is lower than the threshold value, the system may inform the user, via any of the notification types described herein, that the medication needs to be refilled. In one embodiment, the system may automatically send a refill request to the dispensing pharmacy and/or the prescribing physician.

In addition, if a dosage event occurs, e.g., one of the detection buttons 408 was pressed, the attachable device may notify the user, possibly for an extended period of time, to help prevent the user from taking the dose again. For example, the attachable device may light a green LED for, e.g., 5 minutes, or another time configurable by the user.

If the medication container is opened again within a user-defined time (e.g., 5 minutes), this is interpreted as the same dose, and no additional activity information is stored.

In one embodiment, the attachable device may include one or more mood buttons that the user may press to indicate the user's mood and/or how the user is feeling. These buttons may be in addition to the buttons described with respect to FIG. 4 (e.g., buttons 408, 412, 416, 428, and 432), or one or more of the detection buttons 408 may be used for this purpose in addition to indicating the opening of the container.

In one embodiment, there are two mood buttons, one red and the other green (other colors may be used), indicating to the user the function of each button e.g., green for 'feeling good' and red for "feeling bad."

In embodiments where two of the detection buttons double as mood buttons, the system may be configured to interpret a short press of a mood button as a container open signal, and a long press (e.g., 3-10 seconds) of a mood button as signaling the mood of the user. Alternatively, the system may be configured to recognize that the container has been opened when two or more detection buttons are pressed reasonably contemporaneously, and a single button being pressed is used to indicate the user's mood.

The user mood indications, along with the time the button is pressed, are stored in the attachable device until transmitted to the user devices as described herein. The user mood information may be analyzed, aggregated, or otherwise processed for a variety of purposes, including, e.g., determining the effectiveness of the medication and/or medication regimen.

The attachable device may be locatable by the user through a function on the user device. For example, the user may select a locate function through the user interface on the user device, and the user device then tries to detect a beacon signal from the attachable device. If a beacon signal is detected, the user device can determine from the strength of the beacon signal how far away the attachable device is, and guide the user to locating the attachable device. The attachable device may send a beacon signal every 200 to 1000 milliseconds using communication module 210, e.g., using BLE.

While the above process flows have focused on the case of a medication, the same method may be followed for the creation of a regimen involving fluid intake and/or taking vitamin or other nutritional supplements.

Embodiments of the subject matter and the functional operations described in this specification can be implemented in one or more of the following: digital electronic circuitry; tangibly-embodied computer software or firmware; computer hardware, including the structures disclosed in this specification and their structural equivalents; and combinations thereof. Such embodiments can be implemented as one or more modules of computer program instructions encoded on a tangible non-transitory program carrier for execution by, or to control the operation of, data processing apparatus (i.e., one or more computer programs). Program instructions may be, alternatively or additionally, encoded on an artificially generated propagated signal (e.g., a machine-generated electrical, optical, or electromagnetic signal) that is generated to encode information for transmission to suitable receiver apparatus for execution by a data processing apparatus. And the computer storage medium can be one or more of: a machine-readable storage device, a machine-readable storage substrate, a random or serial access memory device, and combinations thereof.

As used herein, the term "data processing apparatus" comprises all kinds of apparatuses, devices, and machines for processing data, including but not limited to, a programmable processor, a computer, and/or multiple processors or computers. Exemplary apparatuses may include special purpose logic circuitry, such as a field programmable gate array ("FPGA") and/or an application specific integrated circuit ("ASIC"). In addition to hardware, exemplary apparatuses may comprise code that creates an execution environment for the computer program (e.g., code that constitutes one or more of: processor firmware, a protocol stack, a database management system, an operating system, and a combination thereof).

The term "computer program" may also be referred to or described herein as a "program," "software," a "software application," a "module," a "software module," a "script," or simply as "code." A computer program may be written in any form of programming language, including compiled or interpreted languages, or declarative or procedural languages, and it can be deployed in any form, including as a standalone program or as a module, component, subroutine, or other unit suitable for use in a computing environment. Such software may correspond to a file in a file system. A program can be stored in a portion of a file that holds other programs or data. For example, a program may include one or more scripts stored in a markup language document; in a single file dedicated to the program in question; or in multiple coordinated files (e.g., files that store one or more modules, sub programs, or portions of code). A computer program can be deployed and/or executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, such as but not limited to an FPGA and/or an ASIC.

Computers suitable for the execution of the one or more computer programs include, but are not limited to, general purpose microprocessors, special purpose microprocessors, and/or any other kind of central processing unit ("CPU"). Generally, CPU will receive instructions and data from a read only memory ("ROM") and/or a random access memory ("RAM"). The essential elements of a computer are a CPU for performing or executing instructions and one or more memory devices for storing instructions and data. Generally, a computer will also include, or be operatively coupled to receive data from or transfer data to, or both, one or more mass storage devices for storing data (e.g., magnetic, magneto optical disks, and/or optical disks). However, a computer need not have such devices. Moreover, a computer may be embedded in another device, such as but not limited to, a mobile telephone, a personal digital assistant ("PDA"), a mobile audio or video player, a game console, a Global Positioning System ("GPS") receiver, or a portable storage device (e.g., a universal serial bus ("USB") flash drive).

Computer readable media suitable for storing computer program instructions and data include all forms of nonvolatile memory, media and memory devices. For example, computer readable media may include one or more of the following: semiconductor memory devices, such as erasable programmable read-only memory ("EPROM"), electrically erasable programmable read-only memory ("EEPROM") and/or and flash memory devices; magnetic disks, such as internal hard disks or removable disks; magneto optical disks; and/or CD ROM and DVD-ROM disks. The processor and the memory can be supplemented by, or incorporated in, special purpose logic circuitry.

To provide for interaction with a user, embodiments may be implemented on a computer having any type of display device for displaying information to a user. Exemplary display devices include, but are not limited to one or more of: projectors, cathode ray tube ("CRT") monitors, liquid crystal displays ("LCD"), light-emitting diode ("LED") monitors and/or organic light-emitting diode ("OLED") monitors. The computer may further comprise one or more input devices by which the user can provide input to the computer. Input devices may comprise one or more of: keyboards, a pointing device (e.g., a mouse or a trackball). Input from the user can be received in any form, including acoustic, speech, or tactile input. Moreover, feedback may be provided to the user via any form of sensory feedback (e.g., visual feedback, auditory feedback, or tactile feedback). A computer can interact with a user by sending documents to and receiving documents from a device that is used by the user (e.g., by sending web pages to a web browser on a user's client device in response to requests received from the web browser).

Embodiments of the subject matter described in this specification can be implemented in a computing system that includes one or more of the following components: a backend component (e.g., a data server); a middleware component (e.g., an application server); a frontend component (e.g., a client computer having a graphical user interface ("GUI") and/or a web browser through which a user can interact with an implementation of the subject matter described in this specification); and/or combinations thereof. The components of the system can be interconnected by any form or medium of digital data communication, such as but not limited to, a communication network. Non-limiting examples of communication networks include a local area network ("LAN") and a wide area network ("WAN"), e.g., the Internet.

The computing system may include clients and/or servers. The client and server may be remote from each other and interact through a communication network. The relationship of client and server arises by virtue of computer programs running on the respective computers and having a client-server relationship to each other.

Various embodiments are described in this specification, with reference to the detailed discussed above, the accompanying drawings, and the claims. Numerous specific details are described to provide a thorough understanding of various embodiments. However, in certain instances, well-known or conventional details are not described in order to provide a concise discussion. The figures are not necessarily to scale, and some features may be exaggerated or minimized to show details of particular components. Therefore, specific structural and functional details disclosed herein are not to be interpreted as limiting, but merely as a basis for the claims and as a representative basis for teaching one skilled in the art to variously employ the embodiments.

The embodiments described and claimed herein and drawings are illustrative and are not to be construed as limiting the embodiments. The subject matter of this specification is not to be limited in scope by the specific examples, as these examples are intended as illustrations of several aspects of the embodiments. Any equivalent examples are intended to be within the scope of the specification. Indeed, various modifications of the disclosed embodiments in addition to those shown and described herein will become apparent to those skilled in the art, and such modifications are also intended to fall within the scope of the appended claims.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

All references including patents, patent applications and publications cited herein are incorporated herein by reference in their entirety and for all purposes to the same extent as if each individual publication or patent or patent application was specifically and individually indicated to be incorporated by reference in its entirety for all purposes.

What is claimed is:

1. A device that removably attaches to a medication container, the device comprising:
    a housing;
    a processor;
    a memory configured to store medication information;
    a notification module;
    one or more single-function detection buttons configured to be pressed in the same motion performed to open the medication container;
    a detection module configured to detect when at least one of the detection buttons is pressed and store at least the time the button is pressed in the memory.

2. The device of claim 1, wherein the device comprises three detection buttons.

3. The device of claim 1, wherein at least one of the one or more detection buttons is disposed at the top of the housing, and at least one of the one or more detection buttons protrudes from the top of the housing by between about 0.70 mm and about 1.15 mm.

4. The device of claim 1, wherein the medication container is configured to be opened using a push and twist motion, and the one or more detection buttons are configured to be pressed during the push and twist motion.

5. The device of claim 1, wherein the housing comprises a diameter of between about 30 mm and about 35 mm.

6. The device of claim 1, further comprising:
    a power source compartment cover configured to removably attach to the housing;
    an adapter, the adapter configured to removably attach to the housing such that the adapter substantially covers the power source compartment cover; and
    a connector configured to attach the adapter to the container.

7. The device of claim 1, wherein the notification module is configured to provide a sequence of at least two user-programmable notifications to a user with respect to a single dose of a medication.

8. The device of claim 1, wherein the notification module is configured to continue to notify a user for a defined amount of time after the opening of the medication container has been detected.

9. The device of claim 1, wherein the detection module is further configured to not store the time a detection button was pressed when the detection button was previously pressed within a defined amount of time.

* * * * *